United States Patent
Weng et al.

(10) Patent No.: US 11,006,879 B2
(45) Date of Patent: May 18, 2021

(54) URINARY BLADDER IRRIGATION DEVICE AND METHOD FOR USING THE SAME

(71) Applicant: National Cheng Kung University, Tainan (TW)

(72) Inventors: Chen-Hsun Weng, Tainan (TW); Ming-Chien Hung, Tainan (TW); Wen-Horng Yang, Tainan (TW); Chien-Hui Ou, Tainan (TW); Ming-Huang Chen, Tainan (TW); Chih-Han Chang, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 162 days.

(21) Appl. No.: 16/256,543

(22) Filed: Jan. 24, 2019

(65) Prior Publication Data
US 2019/0223776 A1 Jul. 25, 2019

(30) Foreign Application Priority Data

Jan. 25, 2018 (TW) ................. 107102757

(51) Int. Cl.
| | | |
|---|---|---|
| *A61B 5/20* | (2006.01) |
| *A61F 5/44* | (2006.01) |
| *A61F 5/442* | (2006.01) |
| *A61B 5/00* | (2006.01) |
| *A61M 39/10* | (2006.01) |
| *A61B 10/00* | (2006.01) |

(52) U.S. Cl.
CPC ............ *A61B 5/208* (2013.01); *A61B 5/6874* (2013.01); *A61B 10/007* (2013.01); *A61F 5/442* (2013.01); *A61F 5/4405* (2013.01); *A61M 39/10* (2013.01); *A61B 5/202* (2013.01); *A61M 2210/1085* (2013.01)

(58) Field of Classification Search
CPC .......... A61B 5/208; A61B 5/207; A61B 5/20; A61B 5/6874; A61B 5/201; A61B 5/6835; A61B 5/6843; A61B 5/6844; A61B 5/6846; A61B 5/6847; A61B 10/007; A61F 5/4405; A61F 5/442; A61F 5/44; A61M 3/02; A61M 3/0204; A61M 3/022; A61M 3/0283; A61M 3/0212; A61M 3/00; A61M 2210/1085; A61M 1/0021; A61M 5/16818; A61M 2209/084; A61M 2209/086

See application file for complete search history.

(56) References Cited

U.S. PATENT DOCUMENTS

| | | | | |
|---|---|---|---|---|
| 2,873,739 A * | 2/1959 | Whann | ............... | A61M 3/0241 604/118 |
| 3,771,522 A * | 11/1973 | Waysilk | ............... | A61M 3/0208 604/28 |
| 2019/0192760 A1* | 6/2019 | Gorbachinsky | ......... | F04B 43/06 |

* cited by examiner

*Primary Examiner* — Kevin C Sirmons
*Assistant Examiner* — Antarius S Daniel
(74) *Attorney, Agent, or Firm* — WPAT, PC

(57) ABSTRACT

A urinary bladder irrigation device includes: a first pipe, a second pipe, a third pipe, a liquid supply member, a liquid collection member, a detection member, and an elevation member. The first pipe has a first opening at one end thereof. The second pipe has a second opening at one end thereof. The third pipe has an end connected to another end of the first pipe and another end of the second pipe and has a third opening at another end thereof. The liquid supply member is connected to the first opening. The liquid collection member is connected to the second opening. The detection member is positioned in the second pipe. The elevation member accommodates the detection member.

9 Claims, 3 Drawing Sheets

US 11,006,879 B2

URINARY BLADDER IRRIGATION DEVICE AND METHOD FOR USING THE SAME

CROSS REFERENCE

This non-provisional application claims priority of Taiwan Invention Patent Application No. 107102757, filed on Jan. 25, 2018, the contents thereof are incorporated by reference herein.

FIELD OF THE INVENTION

The present invention is directed to an irrigation device, and more particularly to a urinary bladder irrigation device and a method for using the same.

BACKGROUND OF THE INVENTION

In the clinically-adoptable urinary bladder irrigation, a liquid, e.g. an irrigating solution, is introduced into a urinary bladder through a catheter, and then extracts out of the urinary bladder to a container through the catheter. After which, a medical personnel collects the liquid in the container to analyze chemical properties thereof so that the irrigation efficiency is determined and also decides whether additional urinary bladder irrigation is required. However, such irrigation may lead to burdens and inconveniences on the irrigation operator. For example, the operator may constantly disassemble the container from the irrigation device or rush forward and backward between the irrigation device and the analyzing device.

Therefore, there is a need to improve the clinically-adoptable urinary bladder irrigation.

SUMMARY OF THE INVENTION

An objective of the present invention is to provide a urinary bladder irrigation device, which can immediately analyze properties of the liquid used in irrigation to immediately obtain the irrigation results. Another objective of the present invention is to provide a urinary bladder irrigation device, which can provide help for urinary bladder control.

Accordingly, the present invention discloses a urinary bladder irrigation device, which includes: a first pipe, a second pipe, a third pipe, a liquid supply member, a liquid collection member, a detection member, and an elevation member. The first pipe has a first opening at one end thereof. The second pipe has a second opening at one end thereof. The third pipe has an end connected to another end of the first pipe and another end of the second pipe and has a third opening at another end thereof. The liquid supply member is connected to the first opening. The liquid collection member is connected to the second opening. The detection member is positioned in the second pipe. The elevation member accommodates the detection member.

Preferably, the first pipe further has a first control valve, and the second pipe further has a second control valve.

Preferably, the detection member is a specific weight measurement device, a pH measurement device, a protein concentration measurement device, a glucose concentration measurement device, a ketone concentration measurement device, a hemoglobin concentration measurement device, a bilirubin concentration measurement device, a urobilin concentration measurement device, a nitrite concentration measurement device, a leukocyte esterase concentration measurement device, or a turbidity measurement device.

Preferably, the detection member is signally connected to the liquid supply member.

Preferably, the urinary bladder irrigation device additionally includes: a metering member connected to the first pipe or positioned in the liquid supply member.

Preferably, the urinary bladder irrigation device further includes: a notification member signally connected to the detection member and/or the metering member.

Preferably, the notification member is a lighting device, an acoustic device, or a shaking device.

Preferably, the urinary bladder irrigation device farther includes: a display member signally connected to the detection member and/or the metering member.

When the urinary bladder irrigation device is used, the third opening is connected to the urinary bladder of an individual (or a catheter opening exposed to the outside of the urinary bladder), and then the elevation member lifts the detection member to a position higher than that of the urinary bladder (or the catheter) to avoid the urine in the urinary bladder from flowing into the liquid collection member. As such, the individual constantly has desire to urinate so as to provide help for urinary bladder control.

When the urine flows to the detection member through the second pipe, the detection member analyzes the urine properties and determines whether the urinary bladder (or the catheter) requires irrigation. If the irrigation is performed, the elevation member lowers the detection member to another position lower than or parallel to that of the urinary bladder (or the catheter). After the liquid supply member provides a liquid into the urinary bladder (or the catheter) for irrigation, the liquid collection member collects the liquid used in irrigation.

When the liquid used in irrigation flows to the liquid collection member through the second pipe, the detection member immediately analyzes the liquid properties. In such a way, it is immediately determined whether additional urinary bladder (or catheter) irrigation is required. Additionally, the structural arrangement saves the liquid collection operation from the liquid collection member and indeed lowers the burdens and inconveniences for irrigation. Moreover, after the irrigation, the elevation member lifts the detection member to the original position for urinary bladder control again.

A further objective of the present invention is to provide a method for urinary bladder irrigation, where properties of the liquid used in irrigation can be immediately analyzed so as to immediately obtain the irrigation results. Yet another objective of the present invention is to provide a method for urinary bladder irrigation, which can provide help for urinary bladder control.

Therefore, the present invention discloses a method for using a urinary bladder irrigation device, which includes the steps of: providing a urinary bladder irrigation device having: a first pipe having a first opening at one end thereof; a second pipe having a second opening at one end thereof; a third pipe having an end connected to another end of the first pipe and another end of the second pipe and having a third opening at another end thereof; a liquid supply member connected to the first opening; a liquid collection member connected to the second opening; a detection member positioned in the second pipe; and an elevation member accommodating the detection member; connecting the third opening to a urinary bladder of an individual or a catheter opening exposed to the outside of the urinary bladder; raising the detection member by the elevation member to a position higher than that of the urinary bladder or the catheter and then analyzing properties of the urine by the detection member to determine whether the urinary bladder or the catheter requires irrigation when the urine in the urinary bladder flows to the detection member through the second pipe; if the irrigation is required, lowering the detection member by the elevation member to another position lower than or parallel to that of the urinary bladder or the catheter; introducing a liquid by the liquid supply member to the urinary bladder or the catheter through the first pipe and the third pipe; collecting the liquid in the urinary bladder or the catheter by the liquid collection member through the third pipe and the second pipe, and then analyzing the collected liquid by the detection member when the liquid flows through the second pipe; and determining whether to repeat the liquid introducing step according to a value obtained in the liquid analyzing step; wherein while the value is out of a pre-determined value, the liquid introducing step is repeated; while the value is within the pre-determined value, the elevation member raises the detection member to the original position again.

Preferably, the detection member is signally connected to the liquid supply member and the elevation member; the detection member lowering step includes: driving the elevation member by the detection member for the detection member lowering; the liquid introducing step includes: driving the liquid supply member by the detection member for the liquid introducing; the repeating determining step includes: while the value is out of the pre-determined value, driving the liquid supply member by the detection member for the liquid introducing, or while the value is within the pre-determined value, driving the elevation member by the detection member for the detection member raising.

Preferably, the urinary bladder irrigation device further includes: a notification member signally connected to the detection member; the repeating determining step includes: notifying by the notification member whether to repeat the liquid introducing step.

Preferably, the urinary bladder irrigation device yet includes: a display member signally connected to the detection member; the liquid collecting step includes: showing by the display member the value obtained in the liquid analyzing step.

Preferably, the urinary bladder irrigation device additionally includes: a metering member connected to the first pipe or positioned in the liquid supply member; the liquid introducing step includes: measuring by the metering member the liquid amount introduced by the liquid supply member.

Preferably, the first pipe further has a first control valve, and the second pipe further has a second control valve; in the liquid introducing step, the first control valve is open, and the second control valve is closed; in the liquid collecting step, the first control valve is closed, and the second control valve is open.

According to the method, before analyzing the urine properties, the arrangement that the detection member is positioned at the higher position than the urinary bladder or the catheter can avoid the urine from directly flowing to the liquid collecting member so that the individual constantly has desire to urinate so as to provide help for urinary bladder control. Additionally, the liquid introducing step can irrigate the urinary bladder or the catheter. After which, when the liquid used in irrigation flows through the second pipe, the liquid properties used in irrigation are immediately analyzed by the detection member. As such, it is immediately determined whether additional urinary bladder irrigation is required. Further, the method saves the liquid collection operation from the liquid collection member and indeed lowers the burdens and inconveniences for irrigation.

Finally, after the irrigation, the elevation member raises the detection member for urinary bladder control again.

DETAILED DESCRIPTION OF THE INVENTION

The detailed description and preferred embodiments of the invention will be set forth in the following content, and provided for people skilled in the art so as to understand the characteristics of the invention.

Figure 1:
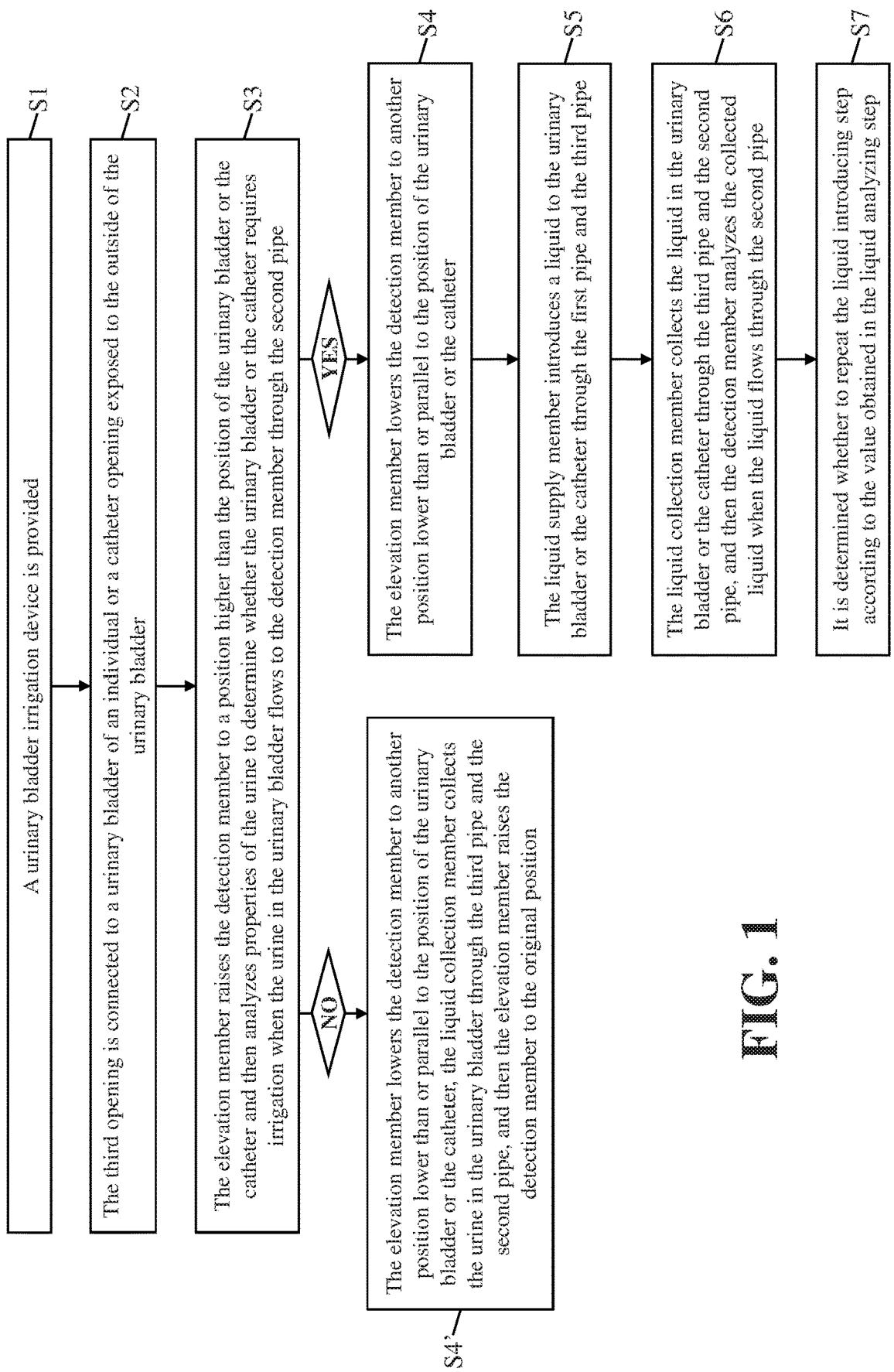
FIG. 1 is a flow diagram illustrating the use of a urinary bladder irrigation device according to an embodiment of the present invention.
Figure 2:
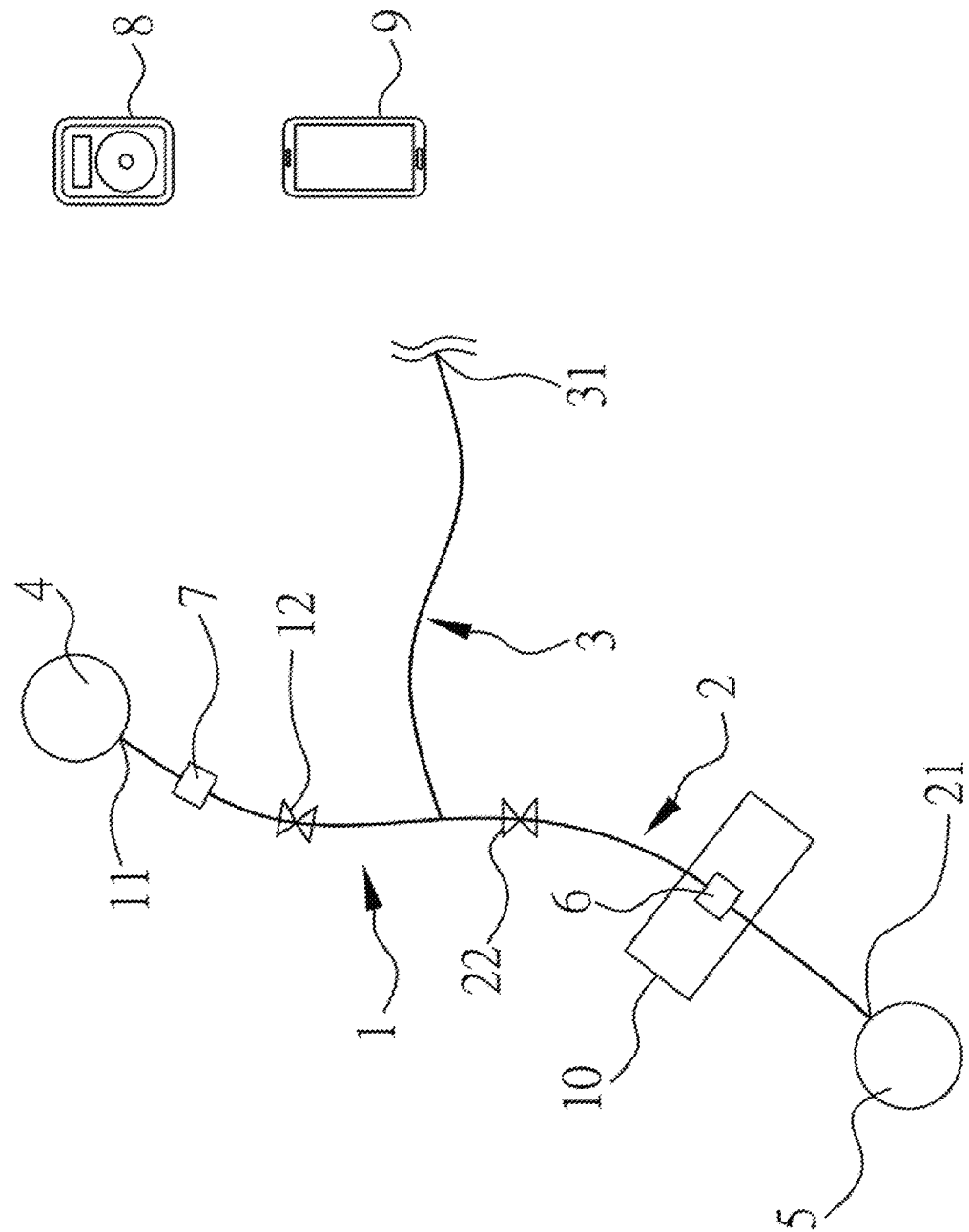
FIG. 2 is a schematic view illustrating the foregoing urinary bladder irrigation device.

With reference to FIG. 1, a method for using a urinary bladder irrigation device according to an embodiment of the present invention is illustrated, and its detailed steps are discussed below:

Firstly, the step (S1) is performed, where a urinary bladder irrigation device is provided. As shown in FIG. 2, the device includes: a first pipe (1), a second pipe (2), a third pipe (3), a liquid supply member (4), a liquid collection member (5), a detection member (6), a metering member (7), a notification member (8), a display member (9), and an elevation member (10).

The first pipe (1) has a first opening (11) at one end thereof. The second pipe (2) has a second opening (21) at one end thereof. The third pipe (3) has an end connected to another end of the first pipe (1) opposite to the first opening (11) and another end of the second pipe (2) opposite to the second opening (21) and the third pipe (3) has a third opening (31) at another end of the third pipe (3). Preferably, the first pipe (1) has a first control valve (12), and the second pipe (2) has a second control valve (22).

The liquid supply member (4) is connected to the first opening (11) of the first pipe (1), and an example thereof is a drip bag or a drip bottle. The liquid collection member (5) is connected to the second opening (21) of the second pipe (2), and an example thereof is a urine bottle, a urine collector, or a urine bag.

The detection member (6) is positioned in the second pipe (2), and an example thereof is a specific weight measurement device, a pH measurement device, a protein concentration measurement device, a glucose concentration measurement device, a ketone concentration measurement device, a hemoglobin concentration measurement device, a bilirubin concentration measurement device, a urobilin concentration measurement device, a nitrite concentration measurement device, a leukocyte esterase concentration measurement device, or a turbidity measurement device.

Figure 3:
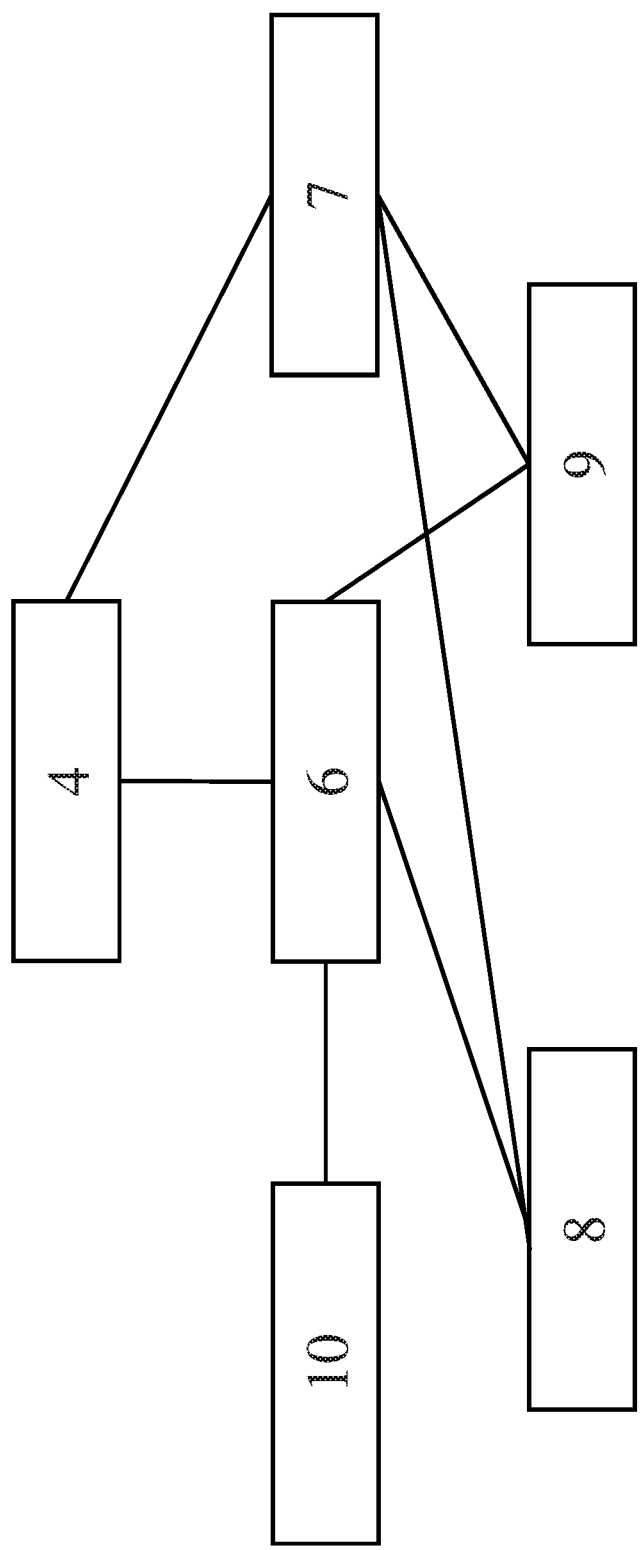
FIG. 3 is a block diagram illustrating the signal connection of the foregoing urinary bladder irrigation device.

As shown in FIG. 3, the detection member (6) is preferably signally connected to the liquid supply member (4). For example, the detection member (6) is connected to the liquid supply member (4) via wired signal connection, e.g. electric wire, wired internet, or universal serial bus (USB); for further example, the detection member (6) is connected to the liquid supply member (4) via wireless signal connection, e.g. radio frequency identification (RFID), wireless fidelity (Wi-Fi), or Bluetooth. The metering member (7) is connected to the first pipe (1) or positioned in the liquid supply member (4), and an example thereof is a weight measurement device or a volume measurement device.

As shown in FIG. 3, the metering member (7) is preferably signally connected to the liquid supply member (4). For example, the metering member (7) is connected to the liquid supply member (4) via wired signal connection, e.g. electric wire, wired internet, or universal serial bus (USB); for further example, the metering member (7) is connected to the liquid supply member (4) via wireless signal connection, e.g. radio frequency identification (RFID), wireless fidelity (Wi-Fi), or Bluetooth.

As shown in FIG. 3, the notification member (8) is signally connected to the detection member (6) and/or the metering member (7), and an example thereof is a lighting device, an acoustic device, or a shaking device. For example, the notification member (8) is connected to the detection member (6) and/or the metering member (7) via wired signal connection, e.g. electric wire, wired internet, or universal serial bus (USB); for further example, the notification member (8) is connected to the detection member (6) and/or the metering member (7) via wireless signal connection, e.g. radio frequency identification (RFID), wireless fidelity (Wi-Fi), or Bluetooth.

As further shown in FIG. 3, the display member (9) is signally connected to the detection member (6) and/or the metering member (7), and an example thereof is a desktop monitor, a notebook monitor, a tablet monitor, or a personal digital assistant (PDA) monitor. For example, the display member (9) is connected to the detection member (6) and/or the metering member (7) via wired signal connection, e.g. electric wire, wired internet, or universal serial bus (USB); for further example, the display member (9) is connected to the detection member (6) and/or the metering member (7) via wireless signal connection, e.g. radio frequency identification (RFID), wireless fidelity (Wi-Fi), or Bluetooth. Additionally, the display member (9) and the notification member (8) may be integrated or separately arranged. The elevation member (10) accommodates the detection member (6).

As further shown in FIG. 3, the elevation member (10) is preferably signally connected to the detection member (6). For example, the elevation member (10) is connected to the detection member (6) via wired signal connection, e.g. electric wire, wired internet, or universal serial bus (USB); for further example, the elevation member (10) is connected to the detection member (6) via wireless signal connection, e.g. radio frequency identification (RFID), wireless fidelity (Wi-Fi), or Bluetooth.

Secondly, the step (S2) is carried out, where the third opening is connected to a urinary bladder of an individual or a catheter opening exposed to the outside of the urinary bladder. It's noted that such connection may be performed with reference to the Foley catherization.

Next, the step (S3) is conducted, where the elevation member raises the detection member to a position higher than the position of the urinary bladder or the catheter, and then analyzes properties of the urine to determine whether the urinary bladder or the catheter requires irrigation when the urine in the urinary bladder flows to the detection member through the second pipe. This step (S3) can avoid the urine from flowing into the liquid collection member so that the individual constantly has desire to urinate so as to provide help for urinary bladder control.

If the irrigation isn't required, the step (S4') is executed, where the elevation member lowers the detection member to another position lower than or parallel to the position of the urinary bladder or the catheter, the liquid collection member collects the urine in the urinary bladder through the third pipe and the second pipe, and then the elevation member raises the detection member to the original position for urinary bladder control again. Conversely, if the irrigation is required, the step (S4) is executed, where the elevation member lowers the detection member to another position lower than or parallel to the position of the urinary bladder or the catheter for performing the following steps. Since the elevation member is signally connected to the detection member, the detection member drives the elevation member for the detection member raising or lowering in the step (S4') or the detection member drives the elevation member for the detection member lowering in the step (S4).

Then, the step (S5) is performed, where the liquid supply member introduces a liquid to the urinary bladder or the catheter through the first pipe and the third pipe. This step (S5) can irrigate the urinary bladder or the catheter with the liquid. As the detection member is signally connected to the liquid supply member, the detection member drives the liquid supply member for introducing the liquid and for automatically executing the irrigation. The first pipe has the first control valve, and the second pipe has the second control valve. The first control valve is open, and the second control valve is closed during introducing the liquid to avoid the liquid from flowing into the liquid collection member. Also during introducing the liquid, the metering member measures the liquid amount introduced by the liquid supply member. Since the display member is signally connected to the metering member, the display member shows the liquid amount introduced by the liquid supply member or the remaining liquid amount in the liquid supply member. Further, since the notification member is signally connected to the metering member, the notification member notifies that the remaining liquid amount in the liquid supply member is sufficient in order to avoid air from flowing into the individual. Further, since the metering member is signally connected to the liquid supply member, when the remaining liquid amount in the liquid supply member is not sufficient, the metering member stops introducing the liquid.

Afterwards, the step (S6) is done, where the liquid collection member collects the liquid in the urinary bladder or the catheter through the third pipe and the second pipe, and then the detection member analyzes the collected liquid when the liquid flows through the second pipe. As described above, the urinary bladder or the catheter is irrigated in the step (S5), and the liquid collected in the step (S6) naturally is a liquid used in irrigation. As such, properties of the liquid used in irrigation are analyzed by the detection member when the liquid flows through the second pipe. On the condition the first pipe has the first control valve, and the second pipe has the second control valve, the first control valve is closed, and the second control valve is open during the liquid collecting to avoid the liquid from backward flowing into the liquid supply member. Additionally, since the display member is signally connected to the detection member, the display member shows an analyzing value.

Finally, the step (S7) is executed where it determines whether to repeat the liquid introducing step according to the value obtained in the liquid analyzing step. Specifically, when the value is out of a pre-determined value, it indicates that the irrigation results are poor and the liquid introducing step should be repeated for further irrigation; when the value is within the pre-determined value, it indicates that the irrigation results are well and the elevation member raises the detection member to the original position again for additional urinary bladder control. Since the elevation member is signally connected to the detection member, the detection member drives the elevation member for raising the detection member again when the value is within the pre-determined value.

The term "pre-determined value" used in the context is chosen by people skilled in this art as demand. For example, while the detection member is the specific weight measurement device, the pre-determined value is of 1.01-1.03. For example, while the detection member is the pH measurement device, the pre-determined value is of pH4.5-8. For example, while the detection member is the protein concentration measurement device, the pre-determined value is of 0-15 mg/dL. For example, while the detection member is the glucose concentration measurement device, the pre-determined value is of 0-100 mg/dL. For example, while the detection member is the ketone concentration measurement device, the pre-determined value is of 0-0.3 mmol/L. For example, while the detection member is the hemoglobin concentration measurement device, the pre-determined value is of 0-3 RBCs/μL. For example, while the detection member is the bilirubin concentration measurement device, the pre-determined value is of 0-0.0005 mg/dL. For example, while the detection member is the urobilin concentration measurement device, the pre-determined value is of 0-0.5 mg/dL. For example, while the detection member is the nitrite concentration measurement device, the pre-determined value is of 0-11 μmol/L. For example, while the detection member is the leukocyte esterase concentration measurement device, the pre-determined value is of 0-2.5 HPF. For example, while the detection member is the turbidity measurement device, the pre-determined value is of 0-100 NTU.

Since the detection member is signally connected to the liquid supply member, when the value is out of the pre-determined value, the detection drives the liquid supply member for introducing another liquid to the urinary bladder or the catheter and for automatically executing irrigation. Additionally, since the notification member is signally connected to the detection member, during the determining, the notification member notifies whether the urinary bladder (or the catheter) requires further irrigation.

As above, the method provided in the embodiment can immediately analyze properties of the liquid used in irrigation to immediately decide whether to require irrigation. Additionally, the method can save the liquid collection operation from the liquid collection member. Therefore, it indeed lowers the burdens and inconveniences for irrigation.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for using a urinary bladder irrigation device, comprising:
    providing a urinary bladder irrigation device having:
        a first pipe having a first opening at one end of the first pipe;
        a second pipe having a second opening at one end of the second pipe;
        a third pipe having a third opening at one end of the third pipe, wherein another end of the third pipe is connected to another end of the first pipe and another end of the second pipe;
        a drip bag or a drip bottle connected to the first opening;
        an urine bottle, a urine collector, or a urine bag connected to the second opening;
        a detection member comprising one of a weight measurement device, a pH measurement device, a protein concentration measurement device, a glucose concentration measurement device, a ketone concentration measurement device, a hemoglobin concentration measurement device, a bilirubin concentration measurement device, a urobilin concentration measurement device, a nitrite concentration measurement device, a leukocyte esterase concentration measurement device, or a turbidity measurement device positioned in the second pipe; and
        an elevation member accommodating and signally connected to the detection member;
    connecting the third opening to a urinary bladder of an individual or an opening of a catheter exposed outside of the urinary bladder;
    raising the detection member by the elevation member to a position higher than that of the urinary bladder or the catheter and then analyzing properties of urine by the detection member to determine whether the urinary bladder or the catheter requires irrigation when the urine in the urinary bladder flows to the detection member through the second pipe;
    if the irrigation is required, lowering the detection member by the elevation member to another position lower than or parallel to that of the urinary bladder or the catheter;
    introducing a liquid by the drip bag or the drip bottle to the urinary bladder or the catheter through the first pipe and the third pipe;
    collecting the liquid in the urinary bladder or the catheter by the urine bottle, the urine collector, or the urine bag through the third pipe and the second pipe, and then analyzing the liquid collected by the detection member when the liquid flows through the second pipe; and
    determining by the detection member whether to repeat the liquid introducing step according to a value obtained in the liquid analyzing step;
    wherein if the value is different from a pre-determined value, the liquid introducing step is repeated; and
    wherein if the value is the same as the pre-determined value, the elevation member raises the detection member to the position higher than that of the urinary bladder or the catheter again.

2. The method as claimed in claim 1, wherein the detection member is signally connected to the elevation member; and
    wherein the step of lowering the detection member comprises: driving the elevation member by the detection member for lowering.

3. The method as claimed in claim 2, wherein the detection member is signally connected to the drip bag or the drip bottle; and
    wherein the determining step comprises: if the value is different from the pre-determined value, driving the drip bag or the drip bottle by the detection member for introducing another liquid to the urinary bladder or the catheter.

4. The method as claimed in claim 3, wherein the determining step comprises: if the value is the same as the pre-determined value, driving the elevation member by the detection member for raising.

5. The method as claimed in claim 1, wherein the urinary bladder irrigation device further comprises: a notification member signally connected to the detection member device; and wherein the determining step comprises: notifying by the notification member whether to repeat the liquid introducing step.

6. The method as claimed in claim 1, wherein the urinary bladder irrigation device further comprises: a display member signally connected to the detection member device; and wherein the liquid collecting step comprises: showing by the display member the value obtained in the liquid analyzing step.

7. The method as claimed in claim 1, wherein the urinary bladder irrigation device additionally comprises: a metering member connected to the first pipe or positioned in the drip bag or the drip bottle; and wherein the liquid introducing step comprises: measuring by the metering member an amount of liquid introduced by the drip bag or the drip bottle.

8. The method as claimed in claim 1, wherein the first pipe has a first control valve, and the second pipe has a second control valve; wherein in the liquid introducing step, the first control valve is open, and the second control valve is closed; wherein in the liquid collecting step, the first control valve is closed, and the second control valve is open.

9. The method as claimed in claim 1, wherein when the liquid collected is analyzed by the weight measurement device, the pre-determined value is 1.01-1.03 mg; wherein when the liquid collected is analyzed by the pH measurement device, the pre-determined value is pH4.5-8; wherein when the liquid collected is analyzed by the protein concentration measurement device, the pre-determined value is 0-15 mg/dL; wherein when the liquid collected is analyzed by the glucose concentration measurement device, the pre-determined value is 0-100 mg/dL; wherein when the liquid collected is analyzed by the ketone concentration measurement device, the pre-determined value is 0-0.3 mmol/L; wherein when the liquid collected is analyzed by the hemoglobin concentration measurement device, the pre-determined value is 0-3 RBCs/µL; wherein when the liquid collected is analyzed by the bilirubin concentration measurement device, the pre-determined value is 0-0.0005 mg/dL; wherein when the liquid collected is analyzed by the urobilin concentration measurement device, the pre-determined value is 0-0.5 mg/dL; wherein when the liquid collected is analyzed by the nitrite concentration measurement device, the pre-determined value is 0-11 µmol/L; wherein when the liquid collected is analyzed by the leukocyte esterase concentration measurement device, the pre-determined value is 0-2.5 HPF; wherein when the liquid collected is analyzed by the turbidity measurement device, the pre-determined value is 0-100 NTU.

\* \* \* \* \*